United States Patent [19]
Pathmanabhan et al.

[11] Patent Number: 5,634,790
[45] Date of Patent: Jun. 3, 1997

[54] VIDEO DENTAL MEDICAL INSTRUMENT

[75] Inventors: Ravi Pathmanabhan; Jason E. Orgain, both of Chico, Calif.

[73] Assignee: Lares Research, Chico, Calif.

[21] Appl. No.: 487,364

[22] Filed: Jun. 7, 1995

[51] Int. Cl.$^6$ .............................. A61C 1/00; A61B 1/00
[52] U.S. Cl. ................................. 433/29; 600/160
[58] Field of Search ................. 433/29, 25; 600/104, 600/109, 112, 136, 156, 157, 160, 169

[56] References Cited

U.S. PATENT DOCUMENTS

| | | |
|---|---|---|
| 4,171,572 | 10/1979 | Nash . |
| 4,398,885 | 8/1983 | Loge et al. ............................ 433/29 X |
| 4,403,956 | 9/1983 | Nakanishi ............................. 433/29 |
| 4,431,412 | 2/1984 | Lares et al. . |
| 4,519,780 | 5/1985 | Strohmaier et al. ................... 433/29 |
| 4,521,189 | 6/1985 | Lares et al. . |
| 4,534,734 | 8/1985 | Lares . |
| 4,614,498 | 9/1986 | Vaccaro . |
| 4,838,246 | 6/1989 | Hahn et al. ........................ 600/157 X |
| 4,966,552 | 10/1990 | Gonser . |
| 5,003,432 | 3/1991 | Mandy . |
| 5,052,924 | 10/1991 | Berg ..................................... 433/29 |
| 5,178,536 | 1/1993 | Werly et al. . |
| 5,512,036 | 4/1996 | Tamburrino et al. ................ 433/29 X |

OTHER PUBLICATIONS

The New 430 Series High Speed Handpieces, Star Dental Division of Den-Tal-Ez, Inc., 1995.

*Primary Examiner*—Jeffrey A. Smith
*Attorney, Agent, or Firm*—John P. O'Banion

[57] ABSTRACT

A dental/medical instrument with an internal imaging or video system wherein the body of the instrument is readily detachable from a connector portion. The instrument preferably contains a swivel feature which allows the body to swivel or rotate 360 degrees relative to the connector, and any hoses or cables attached to the connector, while the instrument is in use. The body of the instrument contains a drill or other operative tool. Illumination is provided to the drill and work area adjacent the tool, and images therefrom are transferred to an imaging system which includes a CCD camera within the instrument.

31 Claims, 12 Drawing Sheets

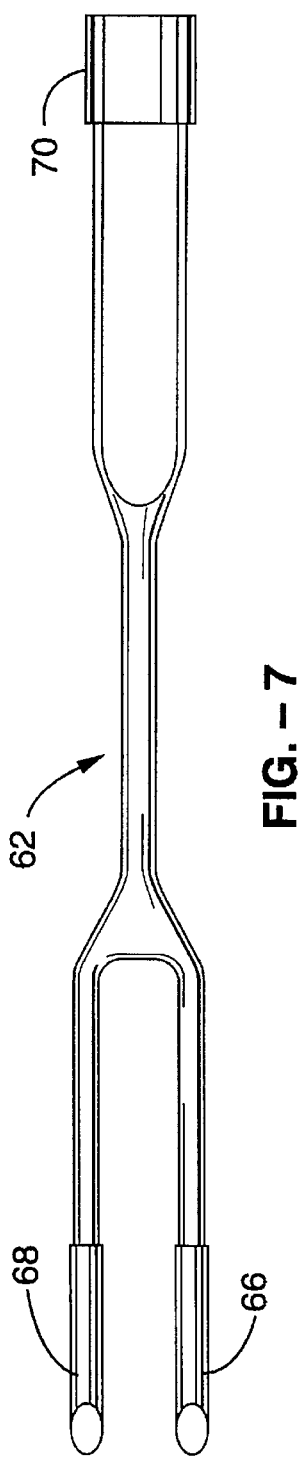
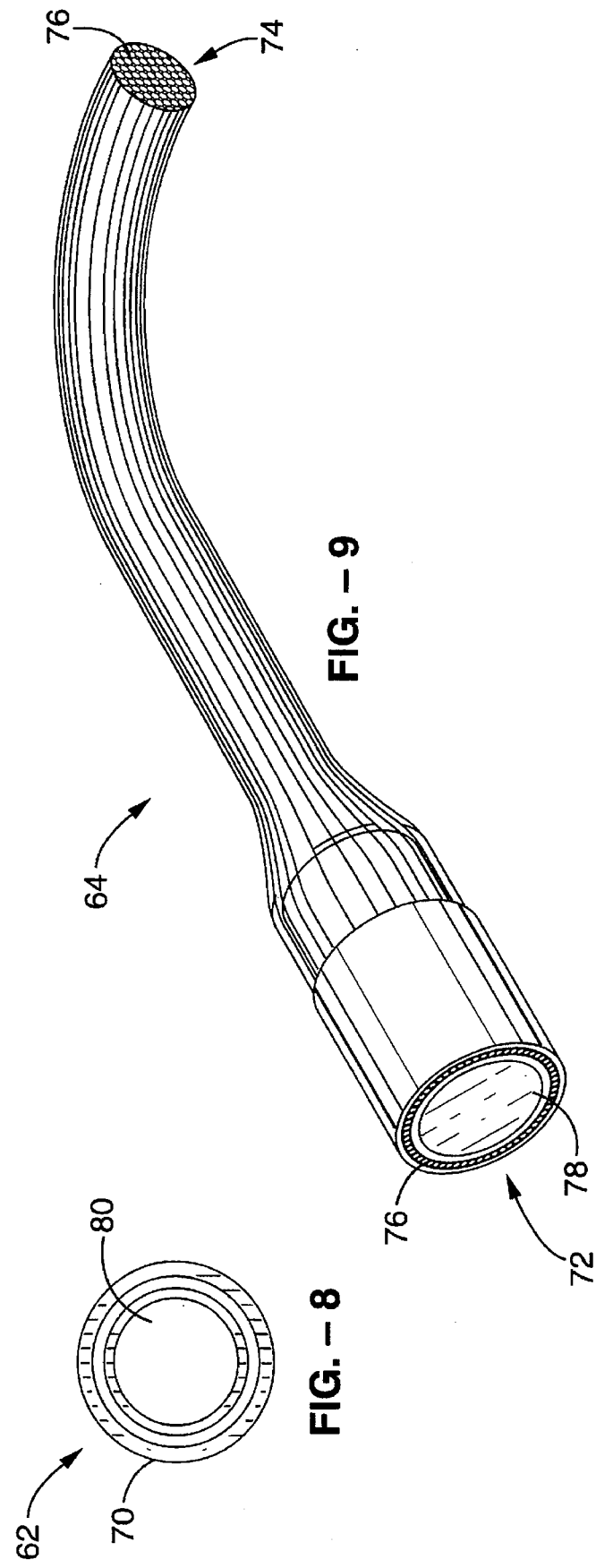

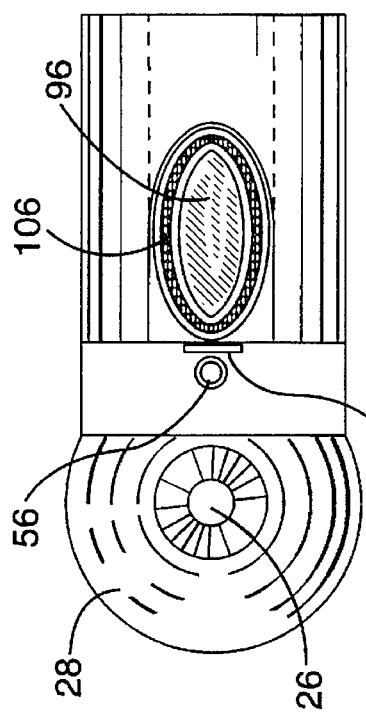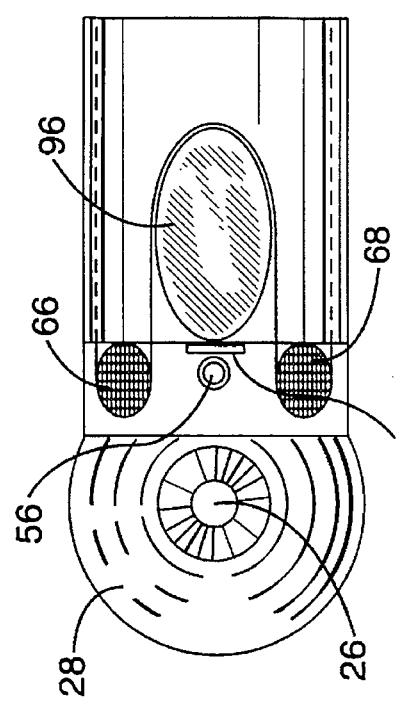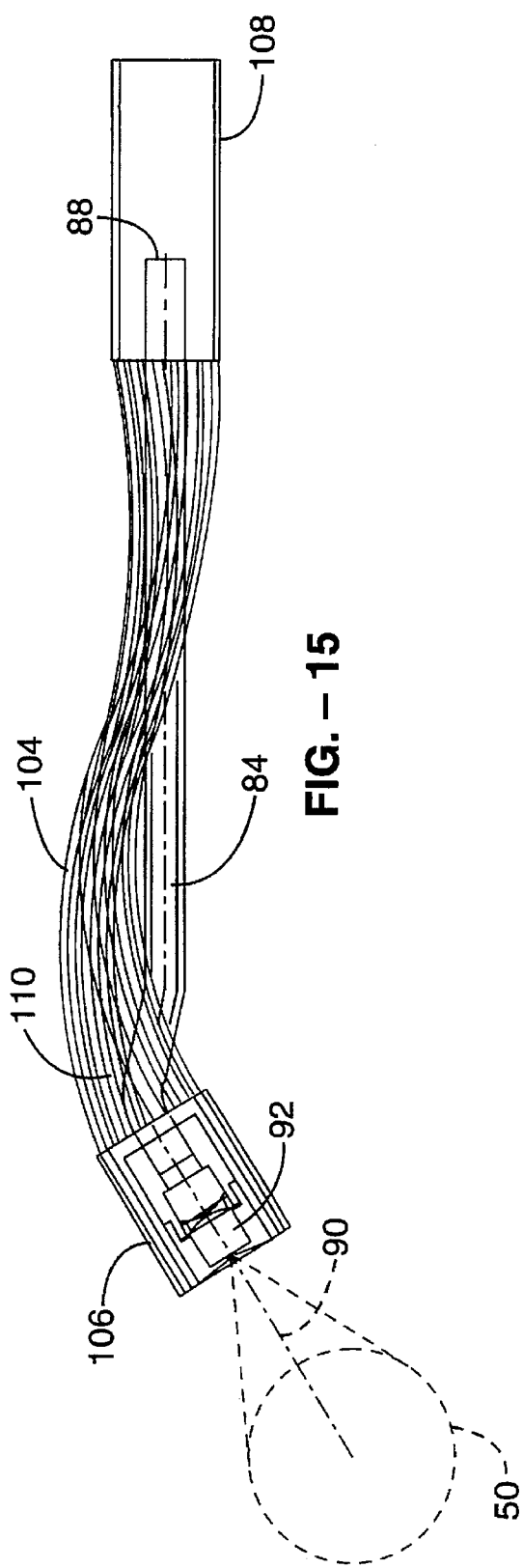

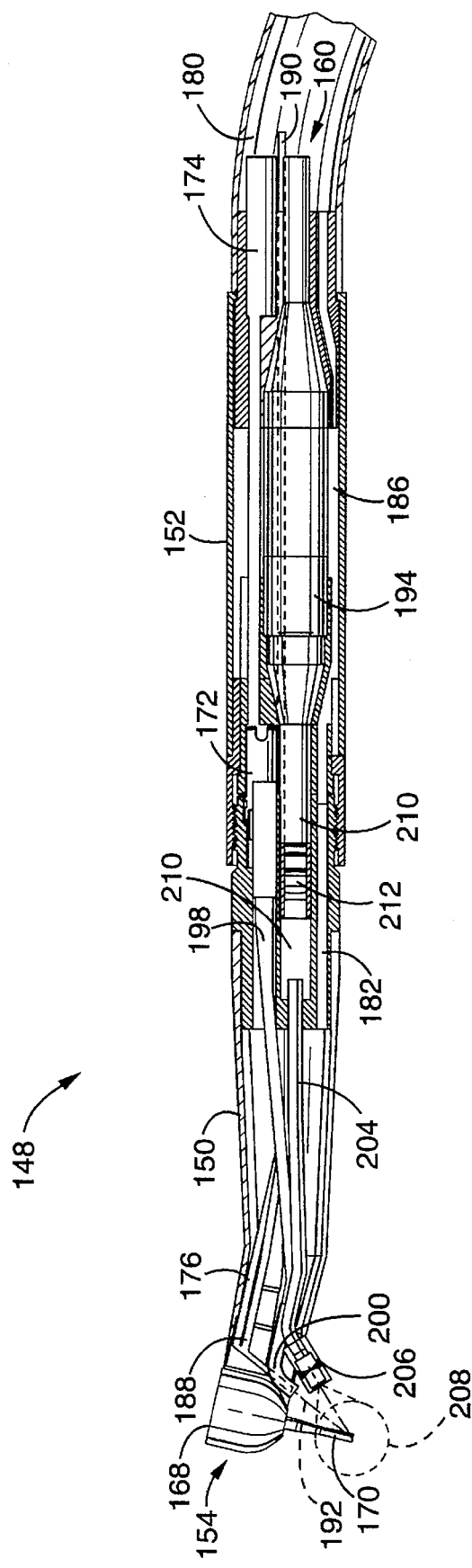
FIG.—17

VIDEO DENTAL MEDICAL INSTRUMENT

BACKGROUND OF THE INVENTION

1. Field of the Invention

The present invention pertains generally to dental and medical instruments which include imaging systems, and more particularly to a dental/medical instrument having an illumination and imaging system which allows for 360 degree rotational motion of the instrument body relative a connector portion.

2. Description of the Related Art

Dental handpieces are commonly used in restorative dental procedures such as removal of decayed or damaged portions of teeth by drilling or abrasion, thereby allowing replacement thereof by metallic or other synthetic filling materials. This type of dental operation is frequently performed in portions of the oral cavity which are not in direct view. Traditionally, dentists have employed small mirrors mounted on handles in order to view the area of the dental operation. Such use of mirrors is difficult and does not always provide a clear view of the operating area. The dentist's view of the operation is further hindered by the water jet accompanying the drill, which tends to mist or otherwise obscure mirror surfaces. Similarly, physicians and other medical personnel must frequently perform procedures in areas which can be hidden by tissue, organs and the like.

Advances in video and endoscopic technology have given rise to the development of dental and medical instruments which include video or other imaging systems which reduce the need for mirrors during dental operations. For example, U.S. Pat. No. 5,178,536 discloses a dentistry set having a head inclined with respect to a drill axis and using visual control, wherein an illuminating head provides light from a fiber optic to the area about a drill bit, and images therefrom are transmitted through a window via mirrors to a CCD camera. U.S. Pat. No. 5,052,924 discloses a fiber optic imaging dental drill in which a fiber optic imaging scope conveys images to a solid state video pickup. U.S. Pat. No. 5,049,070 discloses a dental drill with integral camera and optics which illuminates a work area by fiber optic lens and relays images of the work area to a video imaging device. U.S. Pat. No. 4,917,603 discloses a dental isolation system having a fiber optic illumination and viewing system.

As can be seen therefore, a number of dental tools with illuminating and imaging systems are known. However, such devices suffer from an important drawback in that the handpiece cannot swivel or otherwise rotate relative to an attached supply hose.

Many non-imaging dental handpieces include a swivel feature which allows the handpiece to swivel or rotate during use relative to the attached supply hose. The swivel motion of the hadpiece facilitates access to portions of the oral cavity and reduces stress and fatigue in the hand of the dentist using the handpiece. Various arrangements have been disclosed which allow transmission of air, water, and illuminating light through a swivel connector or swivel feature without interruption during rotation of the handpiece. See, for example, U.S. Pat. Nos. 4,614,498, 4,534,734, 4,512, 189, and 4,431,412, which disclose dental handpieces in which light, air, water, and illumination, but not images, are carried through a swivel connection. Inclusion of such a swivel feature in an imaging or video dental handpiece would require that a fiber optic or other optical communication channel remain interfaced to the imaging system during the rotation or swivelling motion of the handpiece. A transmitted image through such moving parts is easily distorted or destroyed, and is thus difficult to implement. A dental handpiece with an imaging system which provides for 360 degree rotational movement of the body of the handpiece relative to a connector and supply hose has not heretofore been disclosed.

Thus, there is a need for a video dental/medical instrument in which the body of the instrument can swivel or rotate 360 degrees relative to the connecting hose or cable while transmitting undistorted images therebetween, which will not stress or tire the hand of a person using the instrument, and which has a readily detachable and interchangeable body. The present invention satisfies these needs, as well as others, and generally overcomes the deficiencies found in background art dental/medical instruments with imaging systems.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

The present invention pertains to a video dental/medical instrument wherein the body of the instrument is readily detachable from a connector portion, and which provides for the body of the instrument to be rotated 360 degrees during use relative to the connector and any supply hose or cable attached to the connector.

An apparatus in accordance with the present invention comprises a generally elongated body portion having a head for attachment of a dental tool, medical tool, or other operative tool, and a generally elongated connector portion which is detachable from the body portion. The body and connector portions are detachably coupled, and include at their point of coupling a swivel means which provides for rotation of the body and connector portions relative to each other. Included within the body and connector portions is an illumination transferring means for transferring light from a light source located in the connector portion to the work area adjacent to the tool. The body portion also includes an image transferring means for transferring images to an image detection means located either internally or externally to the connector portion.

The illumination transferring means preferably comprises two flexible incoherent fiberoptic bundles, although fused coherent fiberoptic bundles could alternatively be used. One such bundle is contained within the body portion, while the other is located within the connector portion. The fiberoptic bundle in the connector has a tight bundled end adjacent to the light source and a flared annular end adjacent to the swivel means, whereas the bundle in the body has a flared annular end adjacent to the swivel means and a pair of tight bundled ends adjacent to the head of the body in a bifurcated configuration. The flared annular ends of the two bundles are coaxially aligned with the rotational axis of the body and connector, and are in optical communication when the body and connector are joined together to allow transfer of light therebetween. As an alternative to the bifurcated configuration of the fiberoptic bundle in the body, the head end can be a single tight bundled end. As a further alternative, the head end of the bundle in the body can be fashioned into a flared annular end, with the image transferring means coaxially aligned within the flared annular end.

The image transferring means preferably comprises a fused coherent fiberoptic bundle located in the body. One end of the fiberoptic bundle is situated adjacent to the head to receive images from the work area, and the other end is positioned adjacent to coupling end of the body and coaxially aligned with the rotational axes of the body and connector. The image transferring means projects the image into an open coaxial path in the connector. In the preferred embodiment, an objective lens is positioned in the body at the end of the bundle adjacent to the work area, and a focusing lens is positioned in the connector at the coupling end ahead of the image detection means. Alternatively, the focusing lens can be positioned in the coupling end of the body. As a further alternative, a first focusing lens can be positioned in the coupling end of the body, and a second focusing lens positioned adjacent to the imaging means, with an imaging fiberoptic bundle located in the connector between the coupling end and the second focussing lens. With each of these configurations, images are transferred along a coaxial optical path to the imaging means, the coaxial path extending between the body and connector through the swivel means. In this regard, note that the imaging path passes through the coaxial opening in the flared ends of the fiberoptic bundles of the illumination transferring means.

Preferably the imaging means comprises a CCD camera. The CCD camera would then typically be interfaced with an external image processor unit and video display whereby dental operations may be observed by dentist and patient, or medical procedures may be observed by physicians and other medical personnel. Data storage means may be included to store images from dental operations for later reference.

The swivel means for rotatably coupling the body and connector of the apparatus generally comprises a spool and spool body, with the spool located at the coupling end of the connector and the spool body located at the coupling end of the body. Alternatively, the placement of the spool and spool body could be reversed. The spool and spool body are coaxial with the rotational axis of the body and connector, with the spool engaging the spool body in a male-female configuration. Compressed air, exhaust air, water and other fluid (gas or liquid) paths in the body are interfaced respectively with like paths in the connector via the spool body and spool by conventional means. The spool body allows air, exhaust, water and other fluid paths to remain in flow communication while the body is swivelling or rotating relative to the connector. The image and illumination transferring means are preferably coaxial at the coupling ends of the body and connector, and preferably pass through the spool and spool body arrangement.

The image and illumination transfer means as related above may be employed in an apparatus without a swivel feature. In an alternative embodiment of the invention, the illuminating fiber optic bundle pieces and the imaging bundle and optical paths do not require any coaxial location.

An object of the invention is to provide an apparatus having an internal imaging system which permits video monitoring of dental and medical procedures.

Another object of the invention is to provide an imaging instrument in which the body of the handpiece can swivel or rotate 360 degrees relative to a swivel connector and supply hose while the instrument is in use without distortion or disruption of images during rotation.

Another object of the invention is to provide an imaging instrument wherein the video image provided by the imaging system rotates in accordance with the rotation or swivelling of the body of the instrument.

Another object of the invention is to provide an imaging instrument having a quickly detachable and interchangeable portion which can be sterilized.

Another object of the invention is to provide an apparatus which can magnify images of abnormalities or a work area in an oral cavity.

Another object of the invention is to provide an imaging instrument which can access hard to reach places.

Another object of the invention is to provide an imaging instrument having a connector member which is interchangeable with other instruments.

Another object of the invention is to provide a connector member which is interchangeable with a conventional dental non-imaging handpiece.

Further objects of the invention will be brought out in the following portions of the specification, wherein the detailed description is for the purpose of fully disclosing the invention without placing limits thereon.

BRIEF DESCRIPTION OF THE DRAWINGS

The invention will be more fully understood by reference to the following drawings which are for illustrative purposes only:

FIG. 7 is a bottom plan view of a bifurcated fiber optic cable employed as a first fiberoptic illumination bundle in the body portion of the invention shown in FIG. 2.

FIG. 8 is an end view of the flared annular end of the fiber optic cable shown in FIG. 7.

FIG. 9 is a perspective view of an annular fiber optic cable employed as a second fiberoptic illumination bundle in the connector portion of the invention shown in FIG. 4.

FIG. 14 is a bottom plan view of the head portion of the handpiece body shown in FIG. 2 employing the bifurcated fiberoptic illumination cable shown in FIG. 7.

FIG. 15 is a side elevation view in partial cutaway of an alternative embodiment of the imaging and illuminating fiberoptic bundle arrangement of FIG. 10 showing the illumination bundle having a flared annular end adjacent to the head portion of the body.

FIG. 16 is a bottom plan view of an alternative embodiment of the head portion of the handpiece shown in FIG. 14 employing the imaging and illuminating fiberoptic bundle arrangement shown in FIG. 15.

FIG. 17 is a side elevation view in cross-section an alternative embodiment of the dental/medical instrument shown in FIG. 1 wherein the body and connector portions do not swivel.

DETAILED DESCRIPTION OF THE PREFERRED EMBODIMENTS

Referring more specifically to the drawings, for illustrative purposes the present invention is embodied in the apparatus which is generally shown in FIG. 1 through FIG. 21. It will be appreciated that the apparatus may vary as to configuration and as to details without departing from the basic concepts as disclosed herein.

Figure 1:
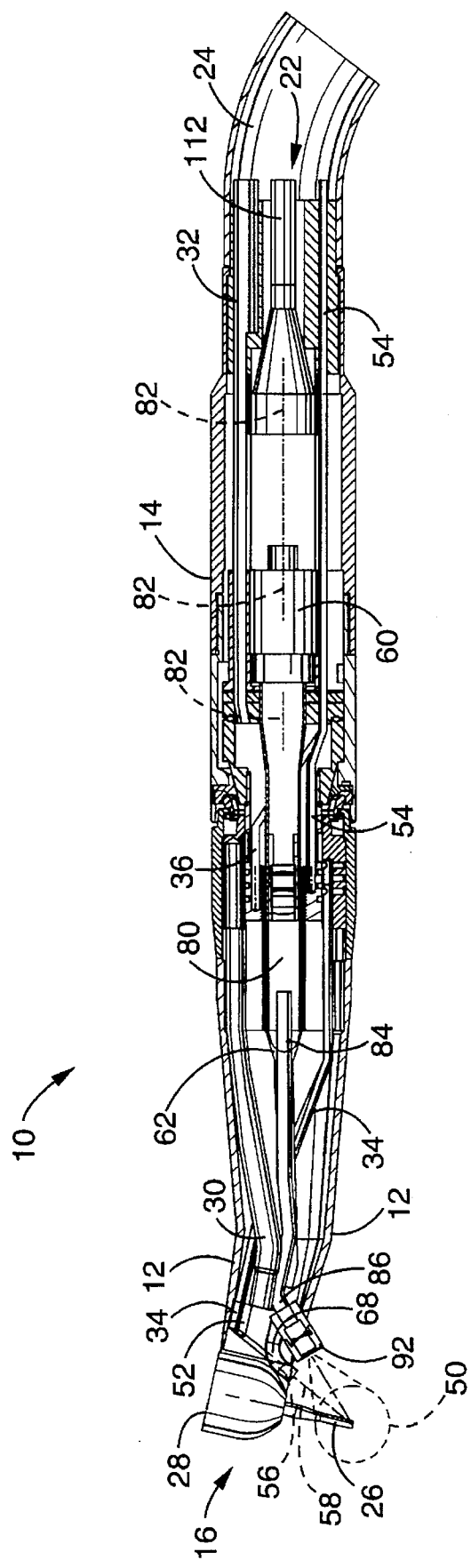
FIG. 1 is a side elevation view in cross-section of a dental/medical instrument in accordance with the present invention providing for rotation of the body portion relative to the connector portion.
Figure 2:
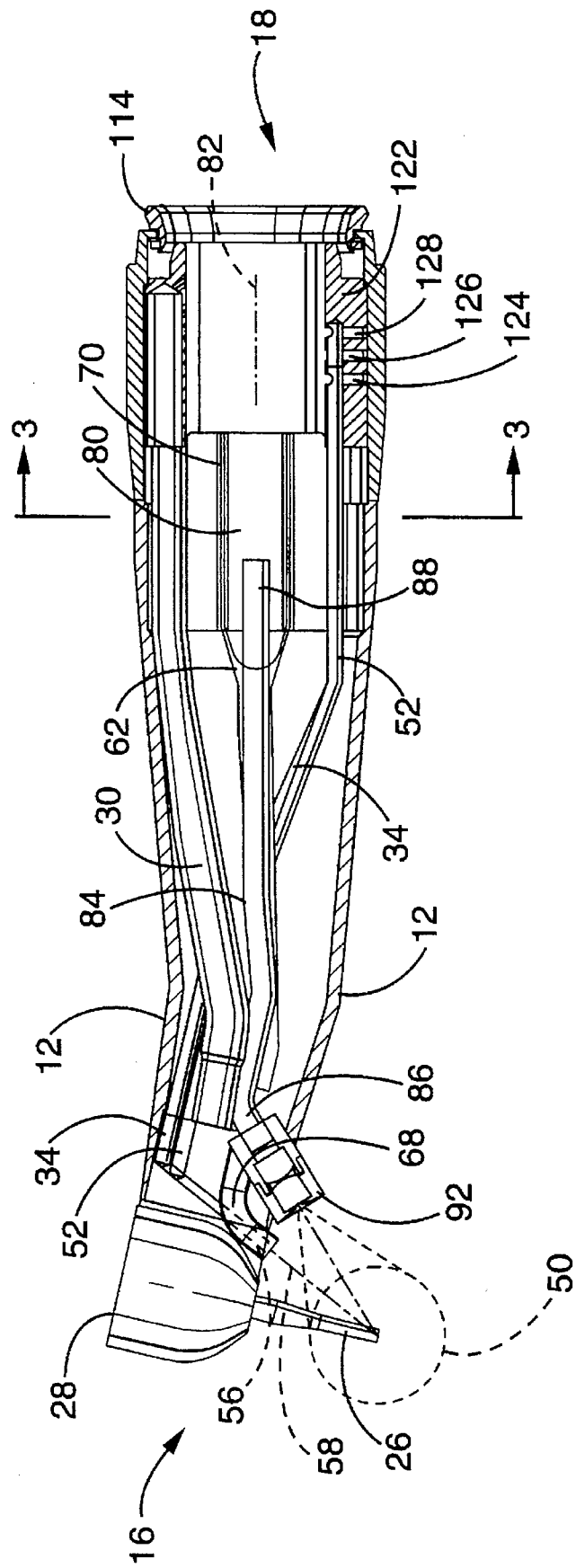
FIG. 2 is a side elevation view in cross-section of the body portion of the dental/medical instrument shown in FIG. 1.
Figure 5:
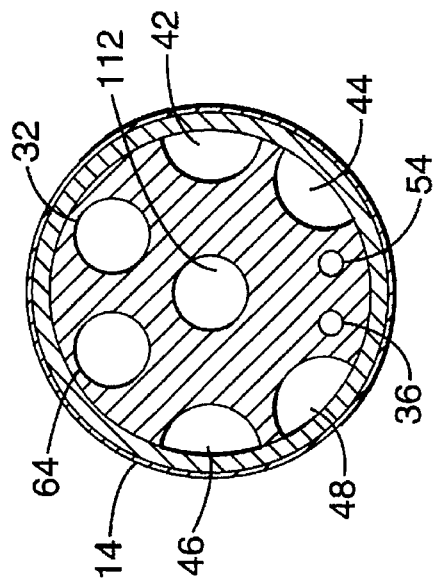
FIG. 5 is a cross-sectional view of the connector shown in FIG. 4 taken through line 5—5.
Figure 21:
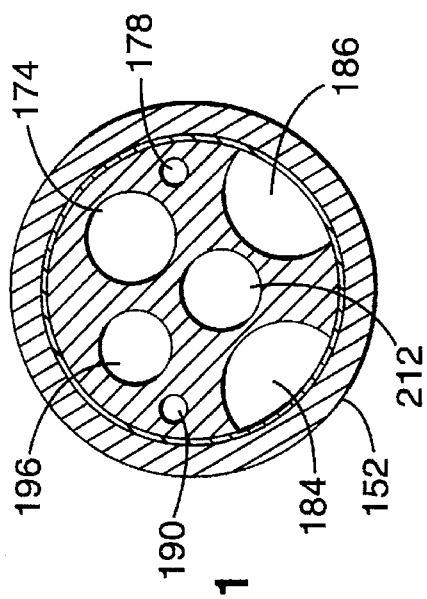
FIG. 21 is cross-sectional view of the connector shown in FIG. 20 taken through line 21—21.
Figure 3:
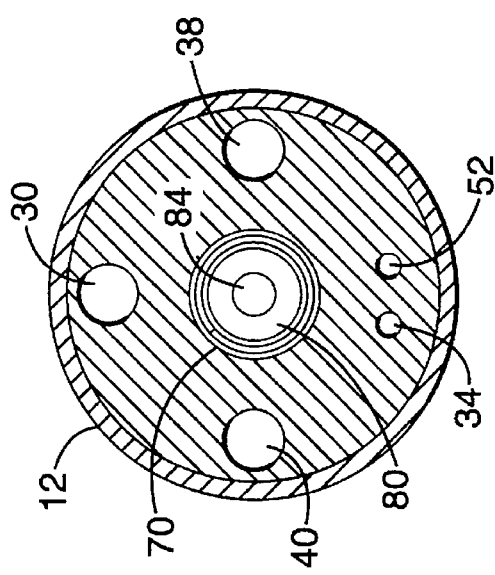
FIG. 3 is cross-sectional view of the handpiece body shown in FIG. 2 taken through line 3—3.
Figure 19:
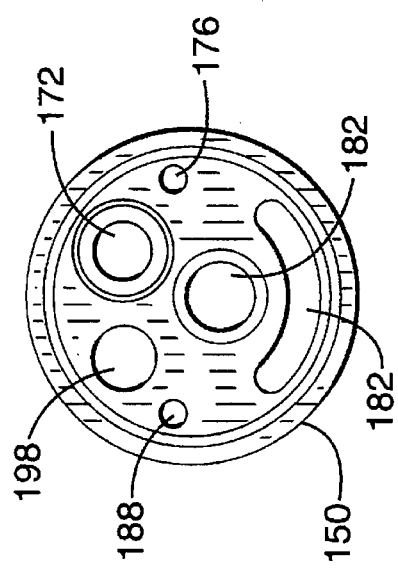
FIG. 19 is an end view of the handpiece body shown in FIG. 18.
Figure 4:
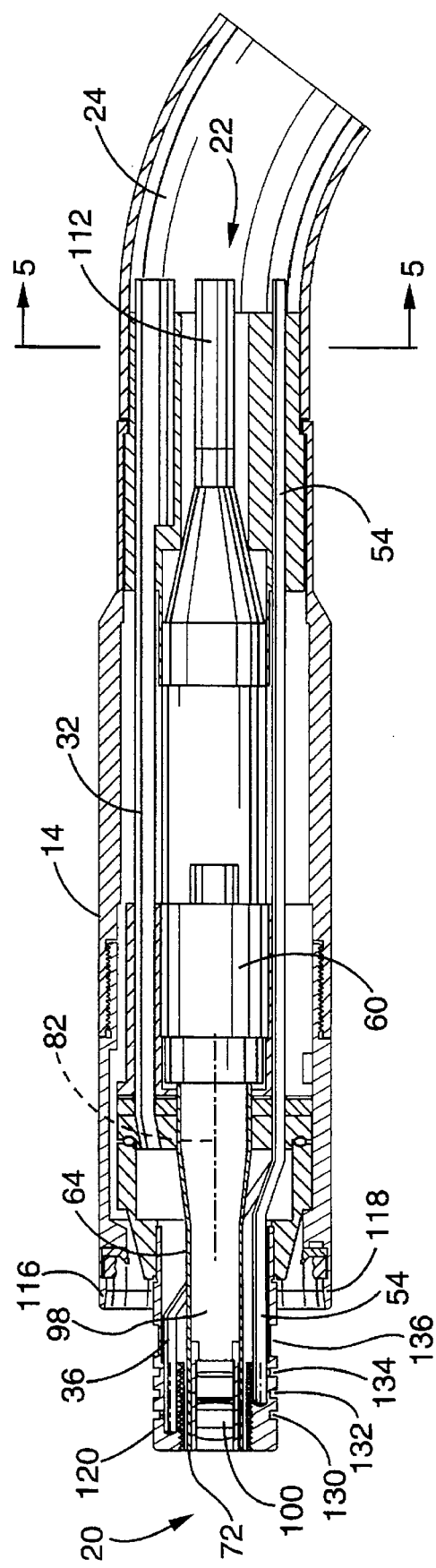
FIG. 4 is a side elevation view in cross-section of the connector portion of the dental/medical instrument shown in FIG. 1.

Referring first to FIG. 1 through FIG. 6, a first embodiment of a dental/medical instrument 10 in accordance with the present invention is generally shown. As shown in FIG. 1, FIG. 2 and FIG. 4, the dental/medical instrument 10 generally comprises an elongated handpiece body portion 12, and an elongated connector portion 14. Body 12 includes a first or proximal end 16, and a second or distal end 18 (FIG. 2). Connector 14 includes a first or proximal end 20 (FIG. 4), and a second or distal end 22. Second end 18 of body 12 is reversibly coupled to first end 20 of connector 14, as discussed below in more detail. A supply hose 24 is coupled to second end 22 of connector 14.

An operative tool 26 such as a drill, bur, laser cutter, aspirator, abrader, or the like is coupled to head 28 adjacent the first end 16 of body 12. Where a rotationally driven tool 26, such as a drill or the like is used, tool 26 can be interchangeable and may be removed from head 28 and replaced with another tool, as is common in the trade. As means for powering tool 26, an electric motor or the like could be included in head 28 for directly driving tool 26, or located in the body with appropriate belts or gears being used to couple the motor to tool 26. If an electric motor is used, it could be powered by an external source of power or by batteries included within the instrument itself. Alternatively, where gas or liquid is used to rotate the tool, head 28 could include a rotational power means such as a conventional turbine coupled to tool 26. Where, for example, the turbine is air-driven, body 12 would include a drive air line 30 and connector 14 would include a drive air line 32, with the drive air lines 30, 32 being in flow communication between body 12 and connector 14 when body 12 and connector 14 are coupled together. If necessary, body 12 can also include an assist air line 34 which is in flow communication with an assist air line 36 in connector 14 when body 12 and connector 14 are joined together. A supply hose 24 would also be included as means for supplying compressed air (not shown) drive air line 32 and assist air line 36 adjacent second end 22 of connector 14. The drive and assist air lines may comprise hoses, tubes, passages, paths, or channels formed within body 12 and connector 14, or any other suitable means for delivering compressed air to the turbine. A plurality of drive air and assist air lines may be included in body 12 and connector 14, and the particular configuration of air lines shown in FIG. 1 through FIG. 5 is merely one of many such arrangements suitable for use with the present invention.

With fluid driven turbines, the handpiece also preferably includes exhaust lines 38, 40 (FIG. 3) in body 12, and exhaust lines 42, 44, 46, 48 (FIG. 5) in connector 14 which are in flow communication when body 12 and connector 14 are engaged. Exhaust from the turbine is received by the exhaust lines and directed away from the handpiece 10 and vented, preferably through suitable exhaust receiving means (not shown) associated with supply hose 24. Exhaust paths 38 through 48 may comprise tubes, hoses, channels, paths, passages, or like means for receiving exhaust from the turbine and directing it to a remote location where it will not interfere with dental operations. Note also that exhaust gas such as air, when the turbine is gas-driven, may also serve as assist air by being directed towards the tool to aid in removal of debris, or to prevent water or other material from interfering with imaging as discussed further below.

Where tool 26 is a rotational tool driven by a turbine or electric motor, dental/medical instrument 10 can include means for directing water to tool 26 to provide cooling to frictionally related surfaces and to aid in removal of loosened debris from the tool 26 and work area 50 adjacent to tool 26. The water directing means preferably comprises a water line 52 in body 12 which is in flow communication with water line 54 in connector 14, when body 12 and connector 14 are engaged. Water supply means (not shown) in supply hose 24 provide water to water lines 52, 54. An orifice or nozzle 56 on water line 52 directs water along path 58 towards tool 26. Many possible configurations and arrangements of water lines are suitable for use with the present invention, and the particular arrangement of the water directing means as shown in FIG. 1 through FIG. 5 is merely illustrative. Water lines 52, 54 may comprise tubes, hoses, channels, paths, passages, or the like.

Imaging means are provided with the present invention to allow the dentist and patient to view tool 26 and work area 50 during dental operations. Preferably, the imaging means comprises a CCD camera 60 or other solid state imaging device or any imaging means commonly used in the endoscopy art. CCD camera 60 is shown as included within connector 14, but may alternatively be located remotely from handpiece 10 and receive images therefrom by fiberoptic or other conventional image transmission means. An image processor (not shown) may also be included. CCD camera 60 is interfaced by suitable means to a remote video display or TV monitor (not shown) whereby dental operations may be observed. Data storage means (not shown) and image printing means (not shown) may be included to store images from dental operations for later reference.

In the preferred embodiment, all fluid paths are arranged within connector 14 so that all fluids provide cooling to CCD camera 60. Water line 54 in connector may also be positioned to provide cooling to CCD camera 60. Providing cooling to CCD camera 60 will improve the signal to noise ratio and increase the quality of the image, as well as increase the useful life of the camera.

The invention includes illumination transferring means for transferring illumination from a light source to tool 26 and work area 50, and image transferring means for transferring images from drill 26 and work area 50 to an imaging means such as CCD camera 60. The illumination and imaging transferring means of the present invention will be more fully understood by referring also to FIG. 7 through FIG. 11 as well as FIG. 1 through FIG. 6.

Referring more particularly to FIG. 7 through FIG. 9, the illumination transferring means preferably comprises a first illuminating fiberoptic bundle 62 in body 12, and a second illuminating fiberoptic bundle 64 in connector 14. First and second illuminating bundles 62, 64 are preferably flexible, incoherent type fiberoptic bundles, but could alternatively be a fused coherent fiberoptic bundle. As seen most clearly in FIG. 7, first illuminating bundle 62 includes a first illumination branch 66 and a second illumination branch 68 forming a bifurcated end, and a flared annular end 70 opposite illumination branches 66, 68. Referring to FIG. 9, second illuminating bundle 64 includes a flared annular end 72 and a tight bundled or solid end 74. The individual optical fibers 76 in bundle 64, which are bunched together at solid end 74, are positionally rearranged along the length of bundle 64 to form a circular or annular arrangement of optical fibers 76 at annular end 72, thereby defining a channel or cavity 78 within annular end 72. Similarly, the individual optical fibers (not shown) in first illuminating bundle 62 are positionally rearranged along the length of bundle 62 from an annular arrangement at annular end 70 into illumination branches 66, 68. A channel or cavity 80 is generally defined within annular end 70. Solid end 74 of second illuminating bundle 64 is interfaced or coupled with a light source, such as a light bulb or other fiberoptic illumination source (not shown) in connector 14 or supply hose 24. It will be appreciated that the light source could be located either within body 12 or connector 14 if desired. For example, the light source could be a small bulb which is located within the body 12 and which is in dynamic contact with the connector 14 to power the bulb.

First illuminating bundle 62 is positioned within body 12, and second illuminating bundle 64 is positioned within connector 14, so that annular end 70 of first illuminating bundle 62 is positioned adjacent second end 18 of body 12, and annular end 72 of second illuminating bundle 64 is positioned adjacent first end 20 of connector 14. Annular ends 70, 72 of first and second bundles 62, 64 respectively are positioned so that they are aligned and optically interface with each other when body 12 and connector 14 are coupled together. Note, however, that the annular ends do not touch so as not to introduce rotational drag. This configuration allows illumination received from solid end 74 of second illuminating bundle 64 to transfer or travel from annular end 72 to annular end 70, and hence to first and second illumination branches 66, 68 of first illuminating bundle 62. First and second illumination branches 66, 68 are positioned adjacent head 28 at body first end 16, and provide dual lighting to tool 26 and work area 50, as seen be seen in FIG. 14. This preferred dual lighting arrangement reduces shadows and optimizes images received from work area 50. Preferably, annular ends 70, 72 of first and second illumination bundles 62, 64 are positioned coaxially relative to the rotational axis 82 of body 12 and connector 14, as shown in FIG. 1 through FIG. 6, so that the relative position and orientation of annular ends 70, 72 will remain fixed during rotational or swivelling motion of body 12 relative to connector 14, allowing illumination transfer during the swivel motion. In other words, when the optical axis of first and second illuminating bundles 62, 64 are coaxial with the rotational axis 82 of body 12 and handpiece 14, uninterrupted illumination transfer occurs over 360 degrees of rotation.

Figure 6:
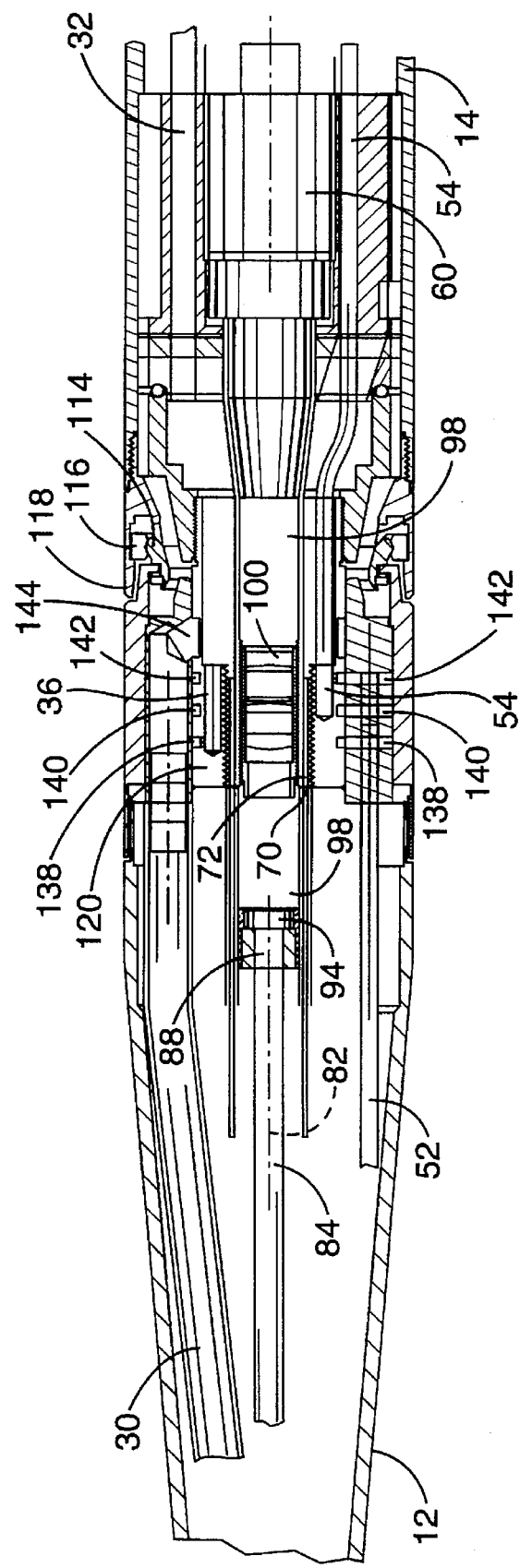
FIG. 6 is a partial side elevation view in cross-section of the dental/medical instrument shown in FIG. 1, showing a detail of the swivel connection and imaging transfer optics.
Figure 10:
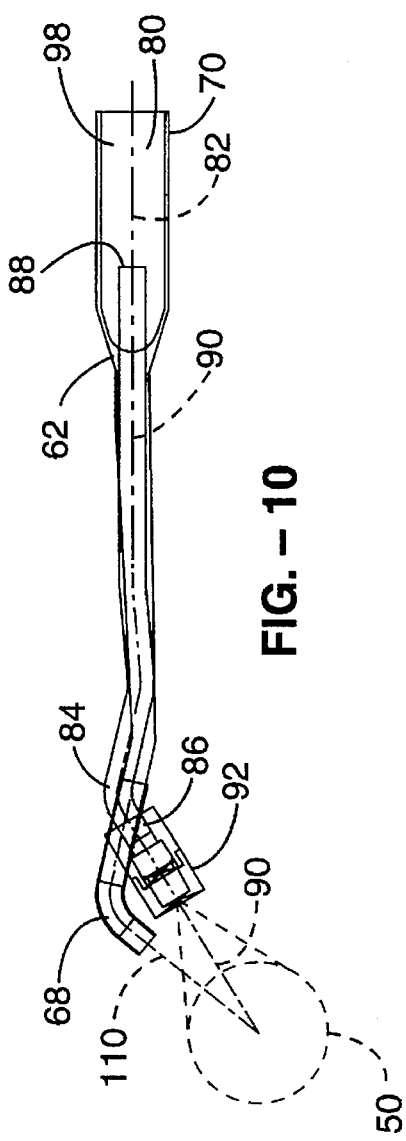
FIG. 10 is a side elevation view in partial cutaway of a preferred arrangement of imaging and illuminating fiberoptic bundles in the handpiece body shown in FIG. 2.
Figure 11:
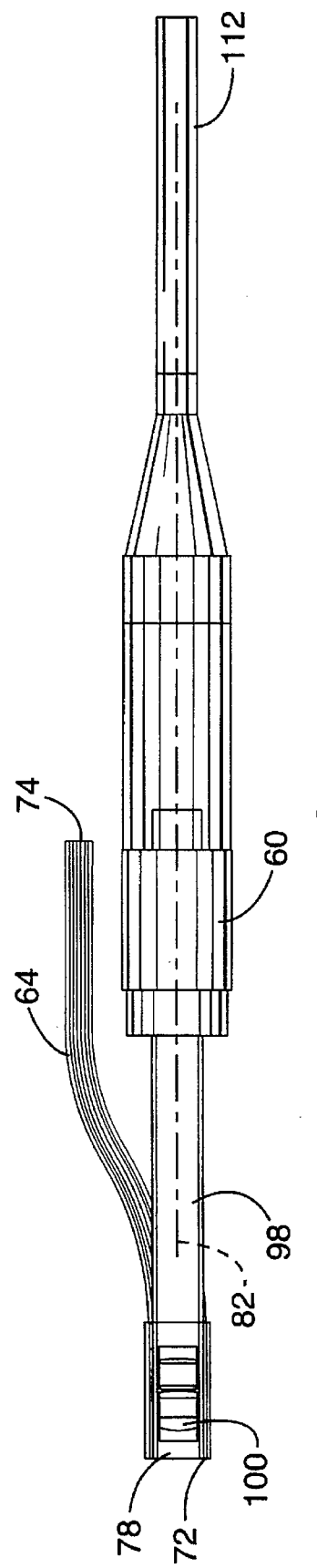
FIG. 11 is a side elevation view of a preferred arrangement for an illuminating fiberoptic bundle and imaging optical path and lens in the handpiece connector shown in FIG. 4.

Referring more particularly to FIG. 6, FIG. 10, and FIG. 11 as well as FIG. 1 through FIG. 5, the preferred image transferring means is generally shown together with the illumination transferring means. The image transferring means generally comprises a fiberoptic imaging bundle 84 included in body 12. Imaging bundle 84 is preferably a fused coherent fiberoptic bundle, but could alternatively be a flexible coherent fiberoptic bundle provided that image alignment can be maintained. Imaging bundle 84 has a first end 86 positioned adjacent tool 26 and work area 50, and a second end 88 positioned adjacent body second end 18. Imaging 84 bundle has an optical axis 90 (FIG. 10), and ends 86, 88 of bundle preferably have surfaces which are perpendicular to the optical axis 90. Note also that the second end 88 of imaging bundle 84 is longitudinally offset from the coupling end of body 12 so as to prevent interference from any light leakage at the flared annular ends of the illumination bundles 62, 64.

An objective lens system 92 is included at first end 86 of imaging bundle 84, and is positioned to receive images from work area 50. Focusing means (not shown) for positionally adjusting objective lens system 92 relative to drill 26 and work area 50 are preferably included with objective lens system 92. An imaging window 94 (FIG. 6) is included on imaging bundle second end 88, and a protective imaging window 96 (FIG. 14) is included adjacent head 28 to protect objective lens system 92 from water spray and debris from work area 50 while allowing transmission of images therethrough.

The image transferring means projects images along an optical path 98, which extends between body 12 and connector 14, as seen most clearly in FIG. 6. Images received by objective lens 92 are transmitted through imaging bundle 84 and along optical path 98 to CCD camera 60. Optical path 98 preferably resides within the channels or hollow portions 78, 80 defined by annular ends 70, 72 of first and second illuminating bundles 62, 64. Optical path 98 is preferably coaxial with rotational axis 82 and CCD camera 60, so that when body 12 and connector 14 are coupled together, images from imaging bundle 84 are transferred along optical path 98. Optical path 98 is coaxial with rotational axis 82, so that images may be transmitted from imaging bundle 84 along optical path 98 during rotational motion of body 12 relative to connector 14 without interruption or distortion of images.

A focusing lens system 100 is positioned in connector 14 along optical path 98 between CCD camera 60 and second end 88 of imaging bundle 84. Referring to FIG. 11, lens system 100 may be included at any point along optical path 98, and is preferably located along optical path 98 within channel 78 at annular end 72 of second illuminating bundle 64 in connector 14. Lens system 100 is coaxial with optical path 98 and rotational axis 82 of body 12 and connector 14. Lens system 100 generally includes conventional optics for fiberoptic transmission, such as a field flattener and a plurality of doublet lenses.

Figure 12:
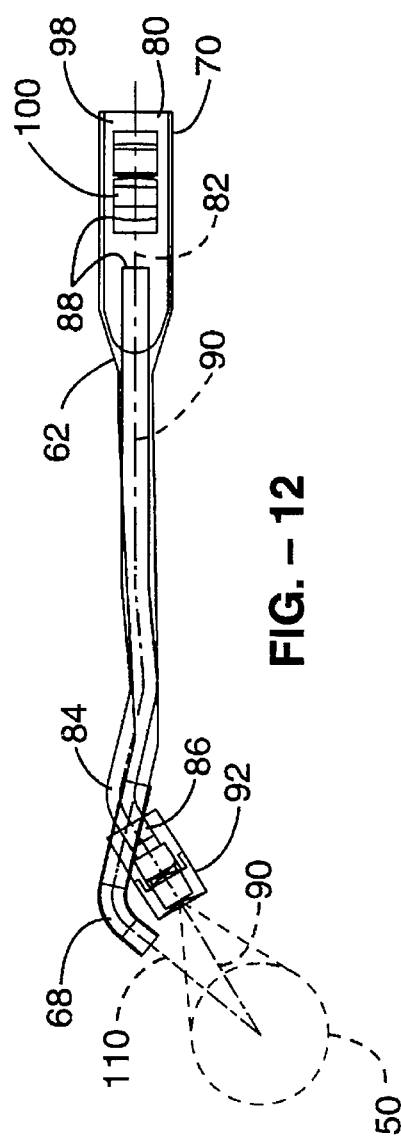
FIG. 12 is a side elevation view in partial cutaway of an alternative embodiment of the fiberoptic arrangement of FIG. 10 shown with an imaging lens positioned in the body portion handpiece body.
Figure 13:
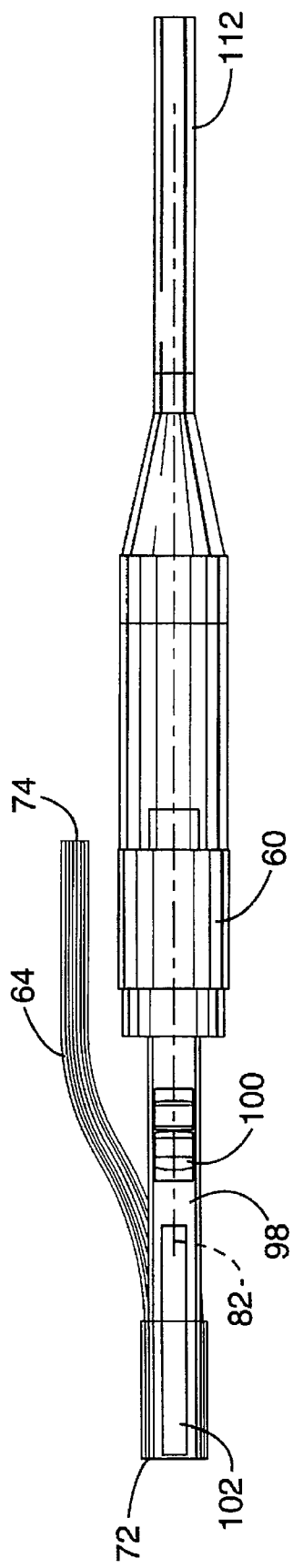
FIG. 13 is a side elevation view of an alternative embodiment of the illuminating fiberoptic bundle and imaging optical path and lens of FIG. 11 shown with a fiberoptic imaging bundle between the end of the connector and the imaging lens.
Figure 18:
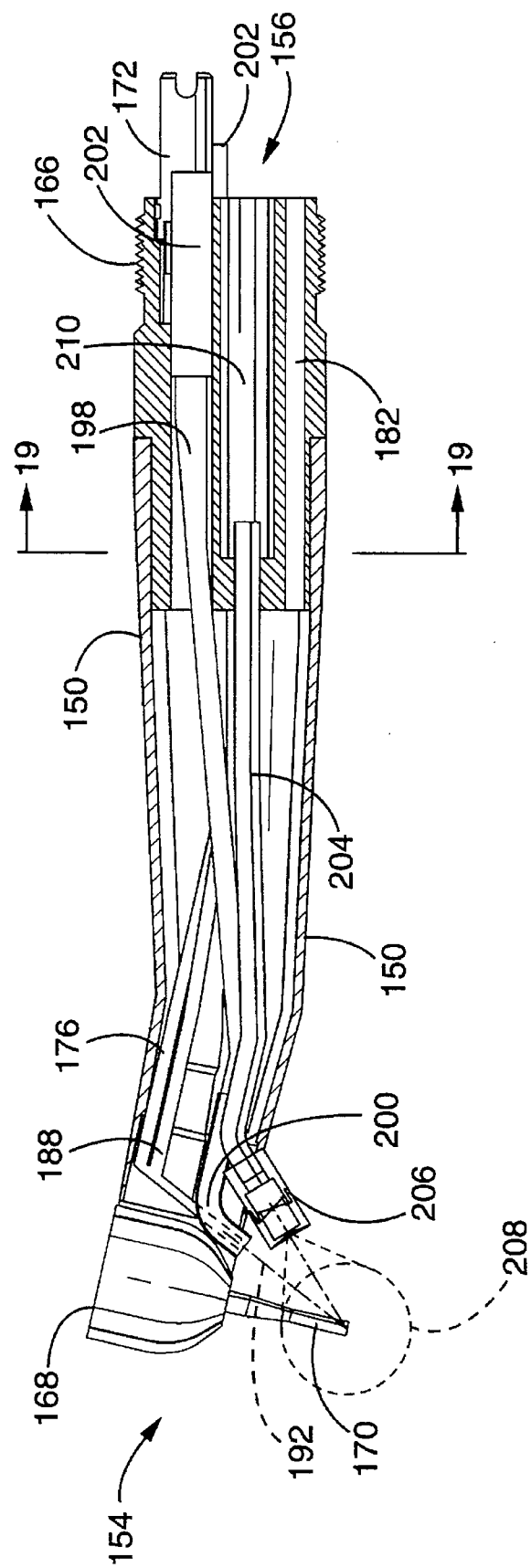
FIG. 18 is a side elevation view in cross-section of the body portion of the dental/medical instrument shown in FIG. 17.
Figure 20:
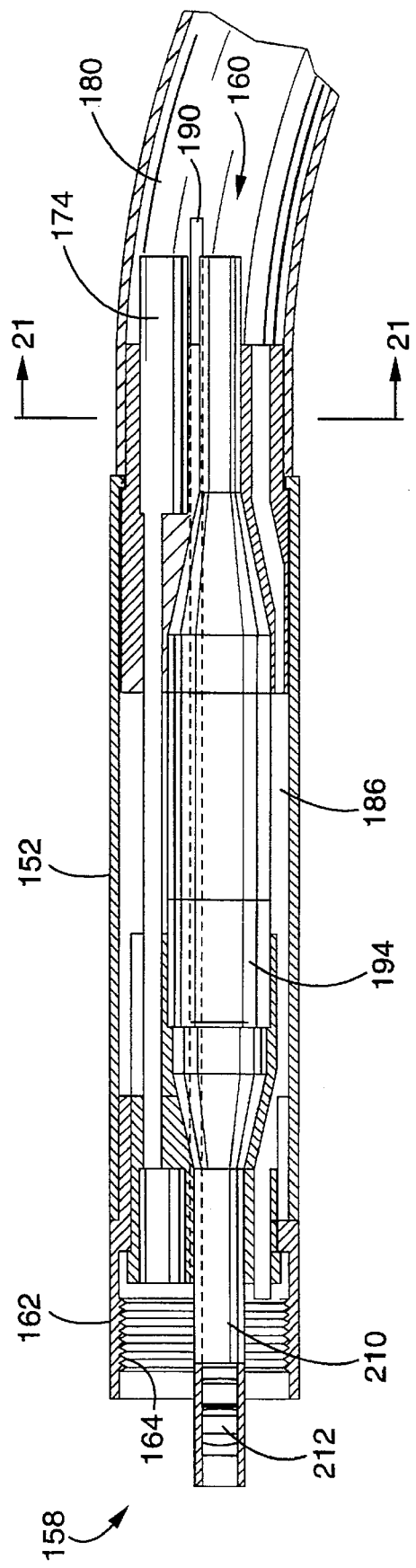
FIG. 20 is side elevation view in cross-section of the connector portion of the dental/medical instrument shown in FIG. 17.

Referring also to FIG. 12 and FIG. 13, alternative embodiments of focusing lens system 100 are shown wherein like reference numerals denote like parts. Referring to FIG. 12, lens system 100 is located in body 12 within cavity 80 in the annular end 70 of illumination bundle 62, and along optical path 98 adjacent to second end 88 of imaging bundle 84. In this embodiment, lens system 100 can be eliminated from the connector instead of positioned as shown in FIG. 11. Or, as can be seen in FIG. 13, a second imaging bundle 102 can be included in connector 14 along optical path 98 between lens system 100 and the end of the connector. Second imaging bundle 102 is preferably a fused, coherent fiberoptic bundle, but may alternatively be a flexible, coherent bundle. Images from imaging bundle 84 are transferred or transmitted along optical path 98 through second imaging bundle 102 to CCD camera 60. As shown in FIG. 13, lens system 100 is included along optical path 98 at a position which is closer to CCD detector 60 than is shown in FIG. 11, in order to accommodate second imaging bundle 102. Those skilled in the art will appreciate that other lens placements are possible. While the optical medium along optical path 98 is preferably air, it is contemplated that vacuum, liquids, fused glass, or other optical media capable of transferring images may comprise the optical medium along optical path 98.

Referring now to FIG. 15 and FIG. 16, there is shown an alternative configuration for the illumination transferring means of the present invention and its positional relationship to the image transferring means, where like reference numerals denote like parts. In this embodiment, body 12 includes a first illuminating bundle 104 having two flared annular ends 106, 108, wherein individual fibers 110 are arranged in a circular or annular fashion at each end 106, 108, of bundle 104. Annular end 108 is positioned adjacent second end 18 of body 14, and annular end 106 is positioned adjacent drill head 28 at body first end 16, so that illumination from annular end 72 of second illuminating bundle 64 in connector 14 is transferred to annular end 108 of bundle 104, and hence to annular end 106. This configuration provides an annular illumination pattern for work area 50, as shown in FIG. 16, with illumination provided in a circular or oval fashion around imaging window 96. The bifurcated illuminating fiber arrangement of FIG. 7, FIG. 10, and FIG. 12 in contrast provides illumination from illumination branches 66, 68 along paths 110 (FIG. 10 and FIG. 12).

It should be readily apparent to persons skilled in the art that the image and illumination transferring means related herein are but a few of many ways and configurations by which images may be transferred from tool 26 to CCD camera 60, and illumination transferred from a light source to tool 26. A plurality of suitably oriented lenses and mirrors along an optical path extending from an area adjacent head 28 to CCD camera 60 could also serve as transferring means for images and illumination without the use of fiber optic bundles. The illumination means could be a light source adjacent to tool 26 and work area 50, or could be included within body 12 and transferred by fiberoptic or other means to work area 50 and tool 26, or the illuminating means could be located remotely and transferred by fiberoptic illuminating bundles 62, 64 as related above in the preferred embodiment. CCD camera 60 is shown generally in FIG. 1 and FIG. 4 as housed coaxially within connector 14, and communicating with a remote video monitor or other display means (not shown) via video link 112 or other electronic or optical communication channel in supply hose 24. CCD camera 60 may alternatively be placed off-center within connector 14, with the image transferring means including mirrors or additional fused or flexible fiberoptic bundles to direct images to CCD camera 60. Other fiber optic bundle arrangements may be used alternatively or in addition to those related above. For example, optical path 98 may alternatively comprise a pair flexible or fused fiber optic bundles which are interfaced at the junction of body 12 and connector 14. Generally, the transferring means will require some coaxial components adjacent the junction of body 12 and connector 14 to allow continuous transfer of images and illumination while body 12 and connector 14 rotate relative to each other.

Referring again to FIG. 1, FIG. 2, FIG. 4 and FIG. 6, the invention preferably includes swivel means for rotatably coupling body 12 to connector 14, so that body 12, and thus tool 26, may be moved 360 degrees relative to connector 14 and supply hose 24. Referring more particularly to FIG. 6 as well as FIG. 2 and FIG. 4, the swivel means preferably comprises an annular swivel ring 114 adjacent second end 18 of body 12, which reversibly engages a snap-on ring 116 on connector first end 20 which is contained generally within an encircling flange 118. Swivel ring 114 and snap-on ring 116 engage or couple in manner which allows facile rotation or swivelling of body 12 relative to connector 14.

The swivel means also comprises a spool 120 on connector first end 20 which rotatably engages a spool body 122 on body second end 18 when connector 14 and body 12 are joined together. Spool 120 could alternatively be included on body second end 18, with spool body placed on connector first end 20. A plurality of inwardly disposed lateral channels 124, 126, and 128 (FIG. 2) are included in spool body 122, and a plurality of outwardly disposed lateral channels 130, 132, and 134 (FIG. 4) are included on spool 120. Spool 120 also includes a lateral groove 136 (FIG. 4) which is parallel to channels 130, 132, and 134. When spool 120 and spool body 122 are engaged, channels 124, 126, 128 in spool body 122 are aligned with channels 130, 132, and 134 respectively of spool 120, so that a plurality of internal lateral passages 138, 140, and 142 (FIG. 6) are formed between spool 120 and spool body 122. Groove 136 in spool 120 abuts spool body 122 to form lateral channel 144 (FIG. 6). Drive air lines 30, 32, assist air lines 34, 36, and water lines 52, 54 remain in flow communication during rotational motion of body 12 relative to connector 14 through the passages thus formed by the engaging or coupling of spool 120 and spool body 122. As shown in FIG. 6, water line 52 in body 12 is in flow communication with water line 54 in connector 14 via passage 142, assist air line 34 in body 12 is interfaced with assist air line 36 in connector 14 through passage 138, and drive air line 30 in body 12 is in communication with drive air line 32 in connector 14 through passage 144. Water line 52 directs water to spray nozzle 56 adjacent to head 28 (FIG. 14, FIG. 16) to create a water spray. As can be seen in FIG. 2, in the preferred embodiment assist air line 34 is in flow communication with water line 52 and the assist air is used for generating the water spray. Additionally, drive air line 32 is preferably tapped and compressed air is directed through air nozzle 146 (FIG. 14, FIG. 16) to provide an air curtain which keeps imaging window 96 clean. Alternatively, exhaust air could be used for the air curtain. It should be readily apparent to persons of ordinary skill in the art, however, that many possible arrangements are possible within spool 120 and spool body 122 for providing flow communication of air and water lines during rotational motion, and the arrangement shown in FIG. 2, FIG. 4, and FIG. 6 is but one of many possibilities within the scope of the present invention.

The image and illumination transferring means preferably pass through spool 120 and spool body 122. As shown in FIG. 4, the annular end 72 of second illuminating fiberoptic bundle 64 passes through spool 120, and lens system 100 is located therewithin. Annular end 70 of first illuminating fiberoptic bundle 62 is coaxially positioned in body 12 relative to spool body 122, so that annular end 70 will interface with annular end 72 of second illuminating bundle 64 when spool 120 and spool body 122 are engaged. When spool 120 and spool body 122 are engaged, images from imaging bundle 84 are transmitted along optical path 98 through spool 120 and spool body 122 to CCD camera 60. Thus, image and illumination transfer, as well as compressed air and water supply, are not interrupted by rotational motion of body 12 relative to connector 14 during dental procedures. The swivel means allows easy manipulation of the handpiece 10 and produces little or no stress on the hand of a dentist using the invention. The swivel feature of the invention also allows quick disconnection of body 12 from connector 14, and replacement with a different instrument. All of the components included in body 12 are preferably made of materials which can be sterilized by autoclaving or other means.

The swivel connection of the present invention makes it easier for a dentist to identify a tooth and orient the handpiece than is possible in conventional dental/medical tools with imaging systems, although it will be appreciated that the swivel means can be eliminated if desired as described below. The present invention provides a true representation of tool to tooth orientation, and a dentist using the invention can use the orientation or position of the tip of tool 26 (when, for example, tool 26 is a drill bit) on the video screen as a pointer since it will always be seen When the body 12 of the invention is positioned with the head 28 and tool 26 pointing towards a particular tooth, the image relayed by the invention to a video monitor is the true representation of the orientation of tool 26 and head 28 relative to the tooth. Rotation of body 12 relative to connector 14 results in a corresponding rotation of the screen image, maintaining a video image of the true orientation of tool 26 and tooth. The tool 26 is in view at all times, and follows the movement of handpiece 10. The tool 26 may thus be used as a pointer or positioning guide when using the invention. The patient as well as the dentist may view the procedure with the present invention.

Referring now to FIG. 17 through FIG. 21, there is shown an alternative embodiment of a handpiece 148 in accordance with the present invention. Handpiece 148 includes an elongated body 150 which reversibly couples to an elongated connector 152. Body 150 includes a first end 154 and a second end 156 (FIG. 18), and connector 152 includes a first end 158 (FIG. 20) and a second end 160. Connector 152 includes an annular sleeve 162 adjacent connector first end 158, with a plurality of inward facing threads 164 on sleeve 162. Body second end 156 includes a plurality of outwardly disposed threads 166 which reversibly engage threads 164 to couple body 150 and connector 152 together. Body 150 includes a head 168 which contains an interchangeable tool 170 or the like. Where a rotating tool 170 is employed, head 168 would include a turbine coupled to tool 170. The turbine would be driven by compressed air or the like flowing through drive air line 174 in body 150 and drive air line 176 in connector 152, with drive air lines 172, 174 in flow communication between body 150 and connector 152 when body 150 and connector 152 are coupled together. Also included is an assist air line or tube 176 in body 150, which is in flow communication with assist air line 178 (FIG. 21) in connector 152 when body 150 and connector 152 are coupled together. Supply hose 180, coupled to connector second end 160, includes means for supplying compressed air (not shown) which is interfaced with drive air line 174. Exhaust path 182 in body 150 interfaces with exhaust paths 184, 186 in connector 152. Exhaust air paths 184, 186 in connector 152 are preferably positioned to provide air cooling to the imaging means. Means for directing water to tool or bur 170 comprises a water line or passage 188 in body 150 which interfaces with water line 190 in connector 152. Water supply means (not shown) in supply hose 180 provide water to water lines 188, 190. An orifice or nozzle (not shown) on water line 188 directs water along path 192 to tool 170.

Imaging means, preferably in the form of a CCD camera 194 (FIG. 17, FIG. 20), are included in connector 152. The imaging means preferably also comprises an image processor and video display (not shown) which are interfaced to CCD camera 194. Illuminating means are preferably provided in the form of an illuminating fiber optic bundle 196 (FIG. 21) within connector 152, which receives illumination from a light source (not shown).

Illumination transferring means are included in the form of fiber optic bundle 198 (FIG. 18) which has a first or bifurcated comprising a first illumination branch 200 and a second illumination branch (not shown). Bundle 198 includes a second end 202 (FIG. 18) which is positioned adjacent body second end 156, so that second end 202 which interfaces with an end (not shown) of illuminating bundle 196 in connector 152. Illuminating bundle 198 is preferably a flexible, incoherent type fiberoptic bundle, but may alternatively comprise a fused, coherent fiberoptic bundle.

Image transferring means is generally included in the form of fiber optic image bundle 204 in body 150, which is coupled to an objective lens system 206 adjacent tool 170 and work area 208. Imaging bundle 204 is preferably a fused coherent fiberoptic bundle, but may alternatively be a flexible coherent fiberoptic bundle. The image transferring means would project an image along an optical path 210 which extends between body 150 and connector 152, with optical path 210 being aligned with CCD camera 194. Lens system 212 directs images from imaging bundle along optical path 210 to CCD camera 194.

The handpiece 102 comprising the alternative or second embodiment of the present invention operates in generally the same manner as the handpiece 10 related above, with the primary exception being the absence of the swivel means present in the first embodiment handpiece 10. Once body 150 and connector 152 are coupled by threading, body 150 remains fixed in position relative to connector 152 and supply hose 180. Since no rotational motion is present, there is no rotational axis, and the image transferring and illumination transferring means do not require coaxial components as in the first embodiment, and need not be coaxial at all. As shown FIG. 17 through FIG. 21, the positions of optical paths 212 is off-center relative to the central axis (not shown) of body 150 and connector 152. Similarly, illuminating fiberoptic bundles 196, 198 are off-center. Since the illumination and image transferring means need not be coaxial with the rotational axis in handpiece 148 of this embodiment, annular fiberoptic bundle ends are not required for illumination transfer. As with the first embodiment of the invention, a number of optical paths and fiber optic configurations and arrangements may be used for the image and illumination transferring means. The transferring means related for the first embodiment could also be used in the alternative embodiment. Similarly, imaging means other than a CCD camera, and illuminating means other than illuminating fiberoptics may be used with handpiece 148. Also, since the alternative embodiment does not include the swivel feature of the first embodiment, the video image obtained by handpiece 148 will always have a downward orientation on the video monitor, even when the tool or bur is pointed upward inside the mouth of a patient. This image could be electronically reversed to display the true orientation of the tool to the tooth.

Accordingly, it will be seen that the present invention provides a dental/medical instrument wherein a body portion is quickly and easily detachable from a connector, and which provides a swivel feature allowing the body to rotate 360 degrees relative to the connector. Although the description above contains many specificities, these should not be construed as limiting the scope of the invention but as merely providing illustrations of some of the presently preferred embodiments of this invention. Thus, the scope of the invention should be determined by the appended claims and their legal equivalents.

What is claimed is:

1. A dental/medical instrument, comprising:
   (a) an elongated body, said body including a first end and a second end;
   (b) an elongated connector, said connector including a first end and a second end, said connector and said body sharing a rotational axis;
   (c) swivel means for rotatably and reversibly coupling said body to said connector, said swivel means included adjacent said second end of said body and said first end of said connector, said swivel means including a spool, said swivel means including a spool body, said spool engaging said spool body, said spool and said spool body positioned coaxially with said rotational axis;
   (d) illumination transferring means for transferring illumination from a light source to a work area adjacent to the instrument;
   (e) image transferring means for transferring an image of said work area through an optical path which is coaxial with the rotational axis of said swivel means; and
   (f) imaging means for detecting said image for visual display or recording thereof.

2. A dental/medical instrument as recited in claim 1, wherein said image transferring means comprises an imaging fiberoptic bundle, said imaging bundle included in said body, said imaging bundle having a first end positioned adjacent to said first end of said body, said imaging bundle having a second end adjacent said second end of said body.

3. A dental/medical instrument as recited in claim 1, wherein said illumination transferring means comprises:
   (a) a first illuminating fiberoptic bundle, said first illuminating bundle included in said body, said first illuminating bundle having a first bifurcated end and a second annular end, said bifurcated end including a first illumination branch and a second illumination branch, said first and second illumination branches positioned adjacent said first end of said body, said annular end positioned adjacent said second end of said body; and
   (b) a second illuminating fiberoptic bundle, said second illuminating bundle included in said connector, said second illuminating bundle including a first annular end positioned adjacent to said first end of said connector, said second illuminating bundle including a bundled end, said bundled end configured for receiving light from said light source.

4. A dental/medical instrument as recited in claim 1, wherein said image transferring means includes first and second ends, and further comprising:
   (a) first lens means for directing images to said image transferring means, said first lens means positioned in said body adjacent to said first end of said image transferring means; and
   (b) second lens means for directing images from said image transferring means to said image means.

5. A dental/medical instrument, comprising:
   (a) an elongated body, said body including a first end and a second end, said body including a compressed air path, said body including an exhaust air path, said body including water supply path;
   (b) a connector, said connector detachably coupled to said body, said connector having a first end and a second end, said connector including a compressed air path interfaced with said compressed air path in said body, said connector including a water supply path interfaced with said water supply path in said body, said connector including an exhaust air path interfaced with said exhaust air line in said body;
   (c) an operative tool;
   (d) rotational power means for rotating said operative tool, said rotational power means coupled to said first end of said body, said compressed air lines positioned to provide air to said rotational power means, said water lines positioned to direct water to said operative tool, said exhaust lines positioned to receive exhaust air from said rotational power means;
   (e) illumination transferring means for transferring illumination from a light source to a work area adjacent to said operative tool;
   (f) image transferring means for transferring an image of said work area through an optical path extending through a coaxial opening in said illumination transferring means; and
   (g) imaging means for detecting said image for visual display or recording thereof.

6. A dental/medical instrument as recited in claim 5, wherein said image transferring means comprises an imaging fiberoptic bundle, said imaging bundle included in said body, said imaging bundle having a first end positioned adjacent to said first end of said body, said imaging bundle having a second end adjacent said second end of said body.

7. A dental/medical instrument as recited in claim 5, wherein said body member and said connector member have a common rotational axis, and further comprising swivel means for rotatably and reversibly coupling said body to said connector, said swivel means included adjacent said second end of said body and said first end of said connector, said swivel means including a spool, said swivel means including a spool body, said spool engaging said spool body, said spool and said spool body coaxial with said rotational axis.

8. A dental/medical instrument as recited in claim 7, wherein said image transferring means passes through said spool and said spool body, said image transferring means is positioned coaxially with said rotational axis adjacent said spool and said spool body, and said illumination transferring means is positioned coaxially with said rotational axis adjacent said spool and said spool body.

9. A dental/medical instrument as recited in claim 5, wherein said illumination transferring means comprises:
   (a) a first illuminating fiberoptic bundle, said first illuminating bundle included in said body, said first illuminating bundle having a first bifurcated end and a second annular end, said bifurcated end including a first illumination branch and a second illumination branch, said first and second illumination branches positioned adjacent said first end of said body, said annular end positioned adjacent said second end of said body; and (b) a second illuminating fiberoptic bundle, said second illuminating bundle included in said connector, said second illuminating bundle including a first annular end positioned adjacent to said first end of said connector, said second illuminating bundle including a bundled end, said bundled end configured for receiving light from said light source.

10. A dental/medical instrument as recited in claim 5, wherein said image transferring means includes first and second ends, and further comprising:

(a) first lens means for directing images to said image transferring means, said first lens means positioned in said body adjacent to said first end of said image transferring means; and (b) second lens means for directing images from said image transferring means to said image means.

11. A dental/medical instrument, comprising:

(a) an elongated body, said body including a first end and a second end, said body including a compressed air path, said body including an exhaust air path, said body including a water supply path;

(b) a connector, said connector detachably coupled to said body, said connector having a first end and a second end, said connector including a compressed air path interfaced with said compressed air path in said body, said connector including a water supply path interfaced with said water supply path in said body, said connector including an exhaust air path interfaced with said exhaust air lines in said body;

(c) an operative tool;

(d) illumination transferring means for transferring illumination from a light source to a work area adjacent to said operative tool;

(e) image transferring means for transferring an image of said work area through an optical path extending through a coaxial opening in said illumination transferring means; and (f) imaging means for detecting said image for visual display or recording thereof.

12. A dental/medical instrument as recited in claim 11, wherein said image transferring means comprises an imaging fiberoptic bundle, said imaging bundle included in said body, said imaging bundle having a first end positioned adjacent to said first end of said body, said imaging bundle having a second end adjacent said second end of said body.

13. A dental/medical instrument as recited in claim 11, wherein said body member and said connector member have a common rotational axis, and further comprising swivel means for rotatably and reversibly coupling said body to said connector, said swivel means included adjacent said second end of said body and said first end of said connector, said swivel means including a spool, said swivel means including a spool body, said spool engaging said spool body, said spool and said spool body coaxial with said rotational axis.

14. A dental/medical instrument as recited in claim 13, wherein said image transferring means passes through said spool and said spool body, said image transferring means is positioned coaxially with said rotational axis adjacent said spool and said spool body, and said illumination transferring means is positioned coaxially with said rotational axis adjacent said spool and said spool body.

15. A dental/medical instrument as recited in claim 11, wherein said illumination transferring means comprises:

(a) a first illuminating fiberoptic bundle, said first illuminating bundle included in said body, said first illuminating bundle having a first bifurcated end and a second annular end, said bifurcated end including a first illumination branch and a second illumination branch, said first and second illumination branches positioned adjacent said first end of said body, said annular end positioned adjacent said second end of said body; and (b) a second illuminating fiberoptic bundle, said second illuminating bundle included in said connector, said second illuminating bundle including a first annular end positioned adjacent to said first end of said connector, said second illuminating bundle including a bundled end, said bundled end configured for receiving light from said light source.

16. A dental/medical instrument as recited in claim 11, wherein said image. transferring means includes first and second ends, and further comprising:

(a) first lens means for directing images to said image transferring means, said first lens means positioned in said body adjacent to said first end of said image transferring means; and (b) second lens means for directing images from said image transferring means to said image means.

17. A dental/medical instrument, comprising:

(a) a body member, said body member including a first end and a second end;

(b) a connector member, said connector member having a first end and a second end;

(c) coupling means for detachably coupling said second end of said body member to said first end of said connector member;

(d) illumination transferring means for transferring illumination from a light source to a work area adjacent to said first end of said body member, said illumination transferring means extending through said body member and said connector member, said illumination transferring means including opposing annular ends adjacent said coupling means, said opposing annular ends having a coaxial opening therethrough;

(e) an imaging fiberoptic bundle extending through said coaxial opening in said illumination transferring means, said imaging bundle having a first end positioned adjacent to said first end of said body member, said imaging bundle having a second end adjacent said second end of said body member; and (f) imaging means for detecting said image for visual display or recording thereof.

18. A dental/medical instrument, comprising:

(a) a body member, said body member including a first end and a second end;

(b) a connector member, said connector member having a first end and a second end;

(c) coupling means for detachably coupling said second end of said body member to said first end of said connector member;

(d) illumination transferring means for transferring illumination from a light source to a work area adjacent to said first end of said body member, said illumination transferring means extending through said body member and said connector member, said illumination transferring means including opposing annular ends adjacent said coupling means, said opposing annular ends having a coaxial opening therethrough;

(e) image transferring means for transferring an image of said work area through an optical path extending through said coaxial opening in said illumination transferring means, said image transferring means including first and second ends;

(f) imaging means for detecting said image for visual display or recording thereof;

(g) first lens means for directing images to said image transferring means, said first lens means positioned in said body member adjacent to said first end of said image transferring means; and (h) second lens means for directing images from said image transferring means to said imaging means.

19. A dental/medical instrument as recited in claim 17 or 18, wherein said coupling means includes swivel means for rotatably coupling said body member to said connector member.

20. A dental/medical instrument as recited in claim 17 or 18, wherein said illumination transferring means comprises:

(a) a first illuminating fiberoptic bundle, said first illuminating bundle included in said body member, said first illuminating bundle having a first end, and an annular second end, said first end positioned adjacent said first end of said body, said annular second end positioned adjacent said second end of said body member; and (b) a second illuminating fiberoptic bundle, said second illuminating bundle included in said connector member, said second illuminating bundle including a first annular end positioned adjacent to said first end of said connector, said second illuminating bundle including a bundled end, said bundled end configured for receiving light from said light source.

21. A dental/medical instrument as recited in claim 20, wherein said body member and said connector member have a common rotational axis, said annular end of said first illuminating bundle positioned coaxially with said rotational axis, said annular end of said second illuminating bundle positioned coaxially with said rotational axis, said first end of said imaging bundle positioned coaxially with said rotational axis, and said optical path positioned coaxially with said rotational axis.

22. A dental/medical instrument as recited in claim 21, wherein said coupling means includes swivel means for rotatably coupling said body member to said connector member.

23. A dental/medical instrument as recited in claims 4, 10, 16 or 18, further comprising means for directing compressed air over said first lens means to keep the optical path free from foreign particles.

24. A dental/medical instrument, comprising:

(a) an elongated body, said body including a first end and a second end;

(b) a connector, said connector detachably coupled to said body, said connector having a first end and a second end;

(c) swivel means for rotatably and reversibly coupling said body to said connector wherein said body and said connector have a common rotational axis, said swivel means included adjacent said second end of said body and said first end of said connector, said swivel means including a spool, said swivel means including a spool body, said spool engaging said spool body, said spool and said spool body coaxial with said rotational axis;

(d) an operative tool;

(e) electric power means for powering said operative tool; illumination transferring means for transferring illumination from a light source to a work area adjacent to said operative tool;

(g) image transferring means for transferring an image of said work area through an optical path; and (h) imaging means for detecting said image for visual display or recording thereof.

25. A dental/medical instrument as recited in claim 24, wherein said image transferring means passes through said spool and said spool body, said image transferring means is positioned coaxially with said rotational axis adjacent said spool and said spool body, and said illumination transferring means is positioned coaxially with said rotational axis adjacent said spool and said spool body.

26. A dental/medical instrument, comprising:

(a) an elongated body, said body including a first end and a second end;

(b) a connector, said connector detachably coupled to said body, said connector having a first end and a second end;

(c) an operative tool;

(d) electric power means for powering said operative tool;

(e) illumination transferring means for transferring illumination from a light source to a work area adjacent to said operative tool, said illumination transferring means comprising (i) a first illuminating fiberoptic bundle, said first illuminating bundle included in said body, said first illuminating bundle having a first bifurcated end and a second annular end, said bifurcated end including a first illumination branch and a second illumination branch, said first and second illumination branches positioned adjacent said first end of said body, said annular end positioned adjacent said second end of said body, and (ii) a second illuminating fiberoptic bundle, said second illuminating bundle included in said connector, said second illuminating bundle including a first annular end positioned adjacent to said first end of said connector, said second illuminating bundle including a bundled end, said bundled end configured for receiving light from said light source;

(f) image transferring means for transferring an image of said work area through an optical path; and (g) imaging means for detecting said image for visual display or recording thereof.

27. A dental/medical instrument as recited in claim 24, 25, 26, wherein said body includes a compressed air path and a water supply path, and wherein said connector includes a compressed air path and a water supply path, said compressed air path in said connector interfaced with said compressed air path in said body, said water supply path in said connector interfaced with said water supply path in said body.

28. A dental/medical instrument as recited in claim 24, 25 or 26, wherein said image transferring means comprises an imaging fiberoptic bundle, said imaging bundle included in said body, said imaging bundle having a first end positioned adjacent to said first end of said body, said imaging bundle having a second end adjacent said second end of said body.

29. A dental/medical instrument as recited in claim 24, 25 or 26, wherein said image transferring means includes first and second ends, and further comprising:

(a) first lens means for directing images to said image transferring means, said first lens means positioned in said body adjacent to said first end of said image transferring means; and (b) second lens means for directing images from said image transferring means to said image means.

30. A dental/medical instrument as recited in claim 29, further comprising means for directing compressed air over said first lens means to keep the optical path free from foreign particles.

31. A dental/medical instrument as recited in claim 5, 11, 17 or 26, further comprising cooling means for cooling heat sensitive elements within said body and said connector.

* * * * *